United States Patent
Windå et al.

(10) Patent No.: US 12,369,807 B2
(45) Date of Patent: Jul. 29, 2025

(54) CAMERA MODULE

(71) Applicant: HJN Sverige AB, Stockholm (SE)

(72) Inventors: Mattias Windå, Vaxholm (SE); Richard Hainzl, Sollentuna (SE)

(73) Assignee: Neko Health AB, Danderyd (SE)

( * ) Notice: Subject to any disclaimer, the term of this patent is extended or adjusted under 35 U.S.C. 154(b) by 6 days.

(21) Appl. No.: 18/566,985

(22) PCT Filed: Jun. 3, 2022

(86) PCT No.: PCT/EP2022/065274
§ 371 (c)(1),
(2) Date: Dec. 4, 2023

(87) PCT Pub. No.: WO2022/263214
PCT Pub. Date: Dec. 22, 2022

(65) Prior Publication Data
US 2024/0267500 A1    Aug. 8, 2024

(51) Int. Cl.
*H04N 13/236* (2018.01)
*A61B 5/0285* (2006.01)
(Continued)

(52) U.S. Cl.
CPC .......... *A61B 5/0285* (2013.01); *A61B 5/0507* (2013.01); *G01S 17/894* (2020.01); *H04N 13/236* (2018.05); *H04N 2213/001* (2013.01)

(58) Field of Classification Search
CPC ............ H04N 13/236; H04N 2213/001; G01S 17/894
(Continued)

(56) References Cited

U.S. PATENT DOCUMENTS 8,279,334 B2   10/2012   Nilson et al.
2008/0079802 A1*   4/2008   Nilson .................. A61B 5/107
                                                 348/44
(Continued)

FOREIGN PATENT DOCUMENTS

JP    2004144727 A  *  5/2004   ............. G01B 11/24
KR    100843473 B1  *  7/2008   ............. G03B 13/36
(Continued)

OTHER PUBLICATIONS

HJN Sverige AB, International Search Report and Written Opinion, PCT/EP2022/065274, Nov. 28, 2022, 17 pgs.
(Continued)

*Primary Examiner* — Behrooz M Senfi
(74) *Attorney, Agent, or Firm* — Morgan, Lewis & Bockius LLP (57) ABSTRACT

The present disclosure relates to a camera module (400). The camera module comprises a 3D modelling device (302) for obtaining respective distances to a plurality of adjacent parts of a surface of a body. The camera module also comprises a camera arrangement for acquiring images of the parts of the surface, wherein the camera arrangement comprises at least one camera (306; 310). Said camera comprises a camera sensor for producing said images, a focusing lens for focusing light reflected on the surface of the body onto the camera sensor, and a movable mirror for sequentially directing light from each of said parts of the surface into the focusing lens. The camera module also comprises a housing (401) enclosing both the 3D modelling device and the camera arrangement. The focusing lens is automatically controllable to set a focus of the camera based on the obtained distances.

15 Claims, 7 Drawing Sheets

(51) Int. Cl.
*A61B 5/0507* (2021.01)
*G01S 17/894* (2020.01)

(58) Field of Classification Search
USPC .......................................................... 348/42
See application file for complete search history.

(56) References Cited

U.S. PATENT DOCUMENTS

2017/0276471 A1     9/2017   Jiang et al.
2018/0313938 A1* 11/2018   Okada .................... H04N 23/60
2020/0121245 A1*   4/2020   Barclay ................ A61B 5/1077

FOREIGN PATENT DOCUMENTS

WO    WO-2005020144 A1 *   3/2005            G06T 7/564
WO    WO-2021175208 A1 *   9/2021            G06V 40/10

OTHER PUBLICATIONS

HJN Sverige AB, International Preliminary Report on Patentability, PCT/EP2022/065274, Jul. 26, 2023, 17 pgs.

* cited by examiner

CAMERA MODULE

CROSS REFERENCE TO RELATED APPLICATION

This Application is a United States National Stage Application filed under 35 U.S.C. § 371 of PCT Patent Application Serial No. PCT/EP2022/065274 filed on Jun. 3, 2022, which claims priority to PCT Patent Application Serial No. PCT/EP2022/062201 filed on May 5, 2022, and to PCT Patent Application No. PCT/SE2021/050608 filed on Jun. 18, 2021, each of which is hereby incorporated by reference in its entirety.

TECHNICAL FIELD

The present disclosure relates to a camera module for obtaining a model of a body.

BACKGROUND

A human body can be non-invasively examined using for example: penetrating photons (x-ray/CT, radio waves), electrical and magnetic fields (MRI), nuclear emissions (PET, Gamma camera), emitted and reflected photons (IR and visible light), ultra-sound (imaging/doppler) and electrical potential (EEG, EKG).

Such techniques are well known and in use. However, several of these techniques require large machines that can only be installed into hospitals or larger clinics. Also, devices using or triggering ionizing radiation like X-rays and PET, cannot be used on a large part of the population due to the side-effects of such radiation.

Speed is also of importance for a modelling system, since the test subject has limited ability to remain still for a longer period of time.

SUMMARY

It is an objective of the present invention to provide an efficient and automated way of modelling a surface of a body by means of a 3D modelling device in combination with a camera.

According to an aspect of the present invention, there is provided a camera module. The camera module comprises a 3D modelling device for obtaining respective distances to a plurality of adjacent parts of a surface of a body. The camera module also comprises a camera arrangement for acquiring images of the parts of the surface, wherein the camera arrangement comprises at least one camera. One or each of said at least one camera comprises a camera sensor for producing said images, a focusing lens for focusing light reflected on the surface of the body onto the camera sensor, and a movable mirror for sequentially directing light from each of said parts of the surface into the focusing lens. The camera module also comprises a housing enclosing both the 3D modelling device and the camera arrangement. The focusing lens is automatically controllable to set a focus of the camera based on the obtained distances.

According to another aspect of the present invention, there is provided a modelling system comprising a frame, and a plurality of the camera modules of the present disclosure, wherein the camera module are fixed in relation to each other on the frame. The modelling system is arranged to receive the body to be modelled.

According to another aspect of the present invention, there is provided a method performed by an embodiment of the camera module of the present disclosure. The method comprises, by the 3D modelling device, obtaining the respective distances to the adjacent parts of the surface of the positioned body. The method also comprises sequentially, for each of the surface parts: automatically moving the mirror to direct light from the surface part into the focusing lens; by the focusing lens, during the moving of the mirror, automatically setting the focus on the surface part based on the obtained distance to said surface part; and, by the camera sensor, acquiring the image of the surface part.

According to another aspect of the present invention, there is provided a computer program product comprising computer-executable components for causing a camera module to perform an embodiment of the method of the present disclosure when the computer-executable components are run on processing circuitry comprised in the camera module.

According to another aspect of the present invention, there is provided a method performed by an embodiment of the modelling system of the present disclosure. The method comprises, by the 3D modelling devices of the camera modules, obtaining a system-wide topographic model of the surface of the body positioned in relation to the modelling system. The method also comprises, based on the obtained topographic model, defining a respective surface section for the at least one camera of each of the camera modules. The method also comprises, to each of the camera modules, sending information about the respective surface section defined for the at least one camera of said camera module.

By including the 3D modelling device and the camera arrangement in the same module, enclosed in a common housing, they are arranged in a fixed spatial relationship to each other, with a known and small parallax between the 3D modelling device and a camera in the camera arrangement. Also, handling is improved by packaging the different devices and cameras in a module which can be handled as a single part. The module can be arranged for modelling a section of the body surface, made up of the plurality of adjacent surface parts. The modelling may include acquiring a full image of the surface of the body, typically stitched together from images acquired of the different parts of the surface, assisted by the distances obtained by the 3D modelling device. The obtained distances may e.g. be used to form a point cloud or other spatial model of the body surface, onto which the acquired images may be overlayed during modelling of the surface of the body. A plurality of modules can easily be arranged on a frame, in a fixed spatial relationship to each other, to form the modelling system, where each module is arranged to model a section of the body surface, where the sections may together cover the whole surface of the body, or a side thereof, e.g. a front side or a back side of the body.

It is to be noted that any feature of any of the aspects may be applied to any other aspect, wherever appropriate. Likewise, any advantage of any of the aspects may apply to any of the other aspects. Other objectives, features and advantages of the enclosed embodiments will be apparent from the following detailed disclosure, from the attached dependent claims as well as from the drawings.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second" etc. for different features/components of the present disclosure are only intended to distinguish the features/components from other similar features/components and not to impart any order or hierarchy to the features/components.

BRIEF DESCRIPTION OF THE DRAWINGS

Embodiments will be described, by way of example, with reference to the accompanying drawings, in which.

DETAILED DESCRIPTION

Embodiments will now be described more fully hereinafter with reference to the accompanying drawings, in which certain embodiments are shown. However, other embodiments in many different forms are possible within the scope of the present disclosure. Rather, the following embodiments are provided by way of example so that this disclosure will be thorough and complete, and will fully convey the scope of the disclosure to those skilled in the art. Like numbers refer to like elements throughout the description.

Figure 1:
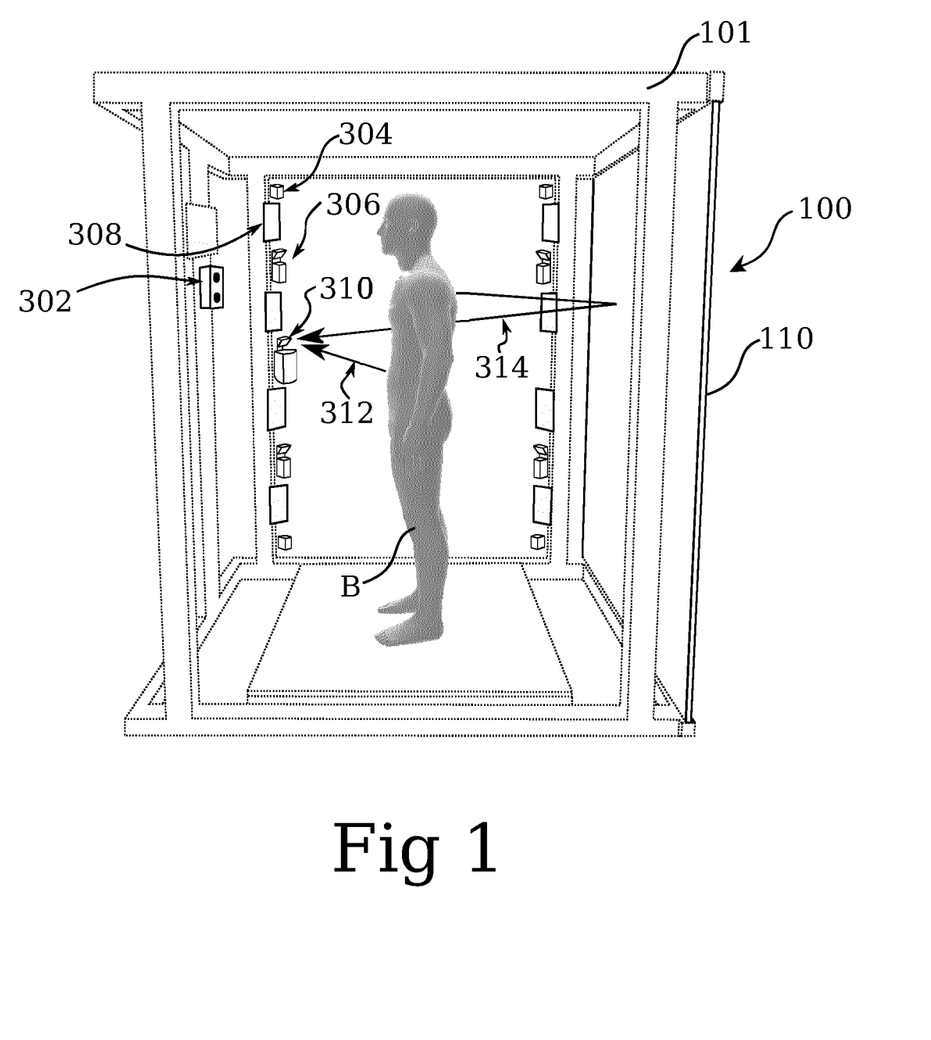
FIG. 1 illustrates how visible-light and thermal cameras may be used, which cameras may be comprised in a camera module in a modelling system 100 for a standing test subject, in accordance with some embodiments of the present invention.

FIG. 1 illustrates how visible and thermal photons can be collected by a modelling system 100 for a standing test subject positioned, preferably immovably, in relation to the modelling system. To simplify the figure, only the cameras and light emitters mounted on the remote pillars of the frame 101 are drawn. In reality any of the pillars or other structural elements of the frame 101 may carry the cameras and/or light emitters. As discussed herein, some or all of a 3D modelling device, e.g. a 3D or depth camera such as a structured-light scanner 302 and/or time-of-flight camera and/or a stereo camera e.g. with a structured light or random dot projector, a visible-light camera 306, typically a colour camera, a thermal camera 310 and/or light emitters 308 may be combined in a camera module 400 (see FIGS. 2 and 3) for improved modelling of a body of a subject. A plurality of modules 400 may be used to cover a larger part of the body B, or the whole body.

A 3D modelling device, e.g. a structured-light scanner 302 (as exemplified herein) and/or a time-of-flight camera and/or a stereo camera or other 3D or depth camera, is used to obtain distances to different parts of a surface of the body B, typically a surface of the skin of a live human or animal body, but possibly at least partly of hair or clothes on top of the skin. These distances may form, or form part of, a spatial 3D model of the body B. The spatial model, e.g. comprising a point cloud, may be acquired using a structured light 3D scanner 302. Such a device 302 comprises a structured light projector and a camera. The camera records the different light patterns projected on the body by the projector and can construct a 3D model, e.g. point cloud, based on this information. An example of such a commercially available camera is the Ajile DepthScan™ 3D imaging system. The structured light 3D scanner is further illustrated in FIGS. 3a and 5.

By means of the spatial model, e.g. comprising or consisting of a point cloud representing the skin surface of the body, any acquired visual-light images, thermal images etc. can be accurately related in space (i.e. spatially) to the body, allowing the body to be modelled with the acquired images. A point cloud can be used, or based upon, by correlating information (images, measurements etc.) to a common coordinate system of the body provided by the point cloud. Such correlated information can then be a source for scheduling camera focus and/or point of view.

The spatial model is limited to the field of view of the 3D modelling device 302. In FIG. 1, a single 3D modelling device 302 is shown. However a plurality of such devices 302, typically in respective camera modules 400, may be positioned, e.g. on all the pillars, around the body to capture the entire body.

It may additionally or alternatively be possible to use a passive model/point cloud acquisition system using multiple wide field of view cameras 304 as 3D modelling devices for obtaining the distances to the surface parts. Using two or more of these cameras 304, it is possible to construct a model/point cloud using photogrammetry analysis.

In another embodiment it is possible to combine 3D model data acquired from the structured light scanner 302 with data from the wide view cameras 304, to create a combined 3D model including the distances to the surface parts. In FIG. 1, the structured light scanner 302 can observe the coronal plane viewing the chest and head areas. The model of the remainder of the body may be covered by the photogrammetry analysis using the wide view cameras 304.

In another embodiment it is possible to use a camera with time-of-flight measurements to acquire the model and thus the distances to the surface parts. Examples of such a camera is the Azure Kinect DK™ depth camera which continuously transmits an amplitude modulated continuous wave in the near infra-red spectrum onto the body and then records the time it takes for the light to travel from the camera to the body and back.

The visual-light camera, e.g. a high-resolution colour camera, 306 may have a narrow field of view and a shallow depth of field designed to take multiple overlapping surface/skin images with a high-resolution. A mirror may be used to select the desired field of view. A focusing device may then be used to take a stack of images using different focal distances for the selected field of view. The stack is then merged into a single image using a focal plane merging algorithm. The camera 306 for the visible light spectrum is further illustrated in FIG. 4a.

The visible-light camera 306 may need a significant amount of lighting to acquire high quality images why separate light emitters 308 may be used, e.g. the LED lighting in the figure.

Thermal camera 310 is an example of a thermal camera. Such a camera may have an appearance similar to the visible-light camera 306, but high-quality thermal cameras are typically larger and significantly more expensive than a high-resolution colour camera. The thermal camera 310 is further illustrated in FIG. 4b.

A thermal camera 310 may view the front of the body B through direct thermal emissions 312, but may additionally or alternatively view the back of the body through a reflection 314 in a glass panel/mirror 110. For a body B of a standing subject, it may be preferable to be able to image both back and front simultaneously. A fast acquisition of thermal images may be important since the subject may move involuntarily when standing. Uncorrected movements can worsen the positional errors and the continuity of testing.

Figure 2:
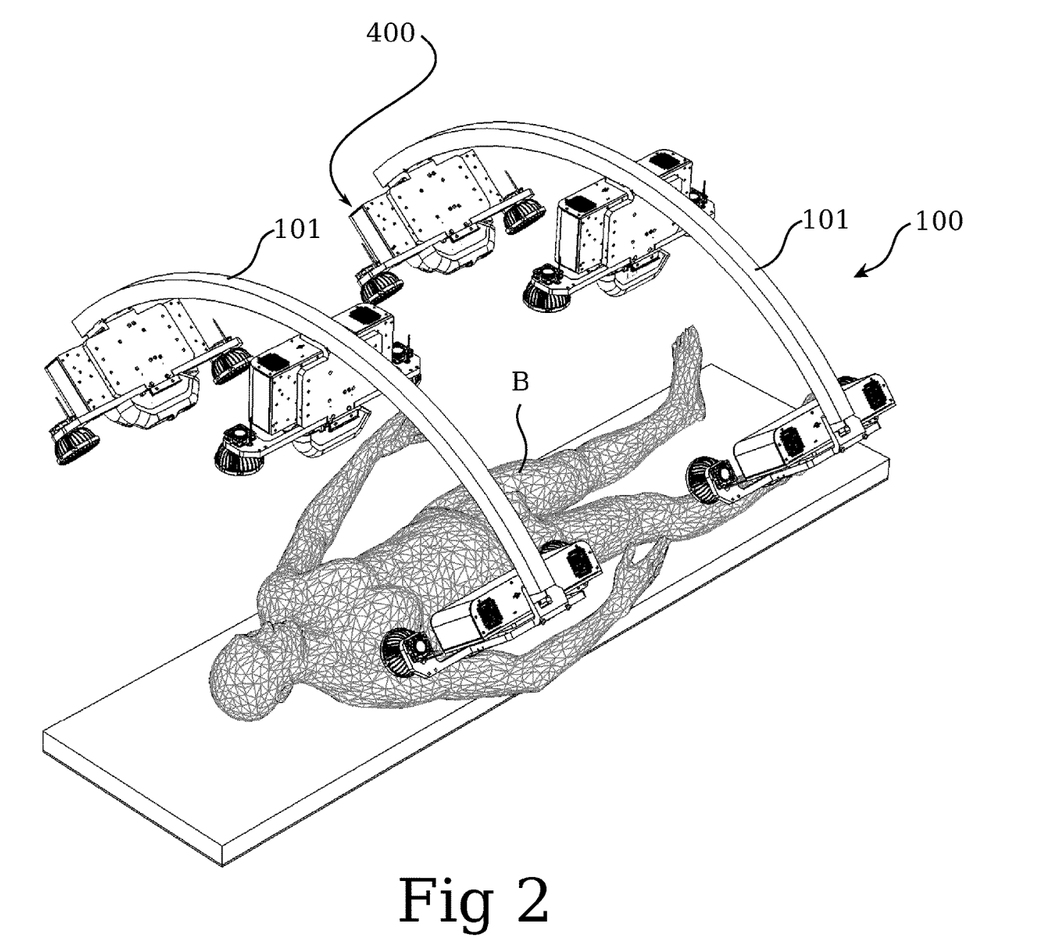
FIG. 2 illustrates how visible and thermal cameras may be enclosed in camera modules 400 in a modelling system 100 for a lying test subject, in accordance with some embodiments of the present invention.

FIG. 2 illustrates how a spatial model, e.g. comprising a point cloud, as well as visible and thermal images may be acquired of a body B by the modelling system 100 for a lying subject. A camera module 400 may contain a light emitter 308, a visible-light camera 306, a thermal camera 310, and/or a structured light scanner 302. A plurality of modules 400 may be used. In the example of FIG. 2, six modules 400 are positioned so as to cover one side (the front) of the body. Typically, during modelling of the body B, i.e. during the obtaining of the distances and during the acquiring of the images, each camera module 400 is arranged a suitable distance from the body, e.g. a distance within the range of 10-100 cm, such as within the range of 30-60 cm. The module, or modules, 400 may be mounted on the frame 101 of the modelling system 100, in a fixed spatial relationship to both the body B and to each other (i.e. to other modules 400 in the modelling system 100).

Figure 3A:
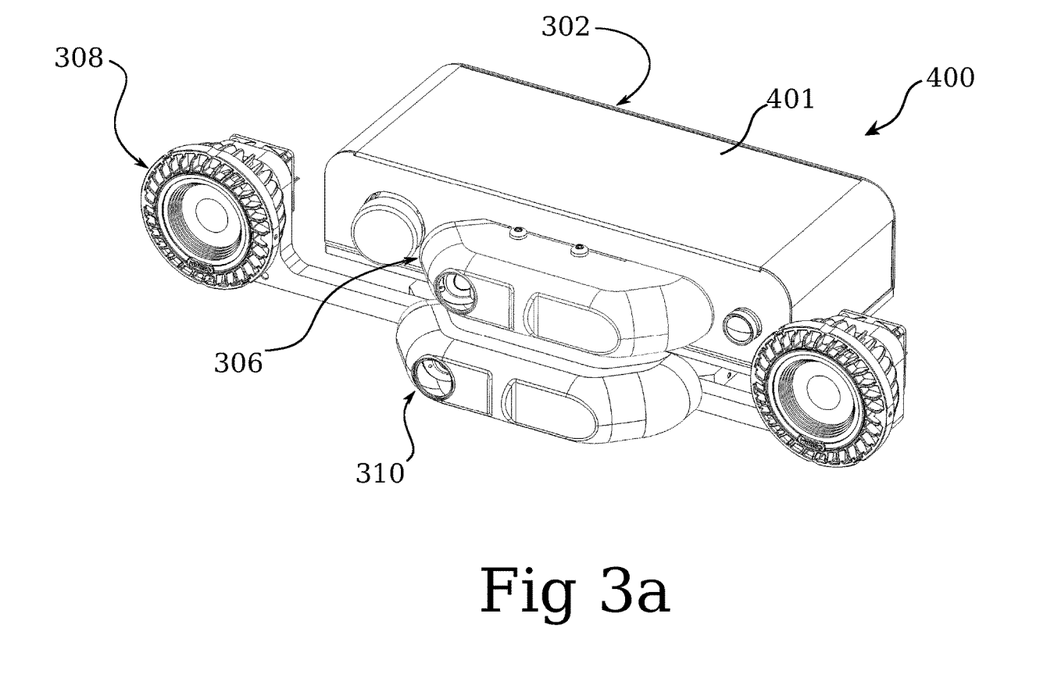
FIG. 3a illustrates an embodiment of a camera module 400, in accordance with some embodiments of the present invention.

FIG. 3a illustrates an embodiment of a camera module 400 for model acquisition. In the example of FIG. 3, the structured light scanner 302 is positioned behind the visible-light camera 306 to minimize the parallax errors between the structured light scanner 302 and the visible-light camera 306. The light emitters 308 may be high-intensity LED light emitters. The thermal camera 310 may be positioned next to the visible-light camera 306. The structured light scanner 302, or other 3D modelling device, as well as the visible-light and/or thermal cameras 306 and 310 are enclosed in a housing 401 of the camera module 400.

Figure 3B:
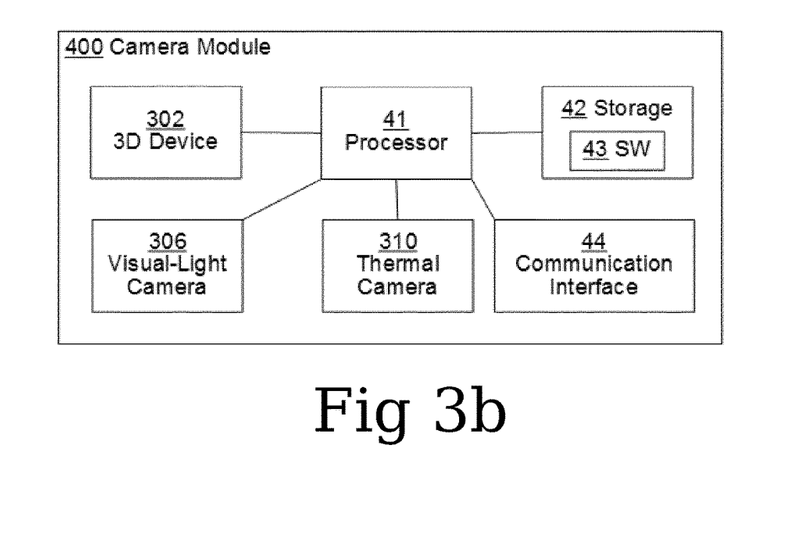
FIG. 3b is a schematic block diagram of a camera module 400, in accordance with some embodiments of the present invention.

FIG. 3b schematically illustrates an embodiment of a camera module 400 of the present disclosure. The camera module 400 comprises processing circuitry 41 e.g. a central processing unit (CPU). The processing circuitry 41 may comprise one or a plurality of processing units in the form of microprocessor(s). However, other suitable devices with computing capabilities could be comprised in the processing circuitry 41, e.g. an application specific integrated circuit (ASIC), a field programmable gate array (FPGA) or a complex programmable logic device (CPLD). The processing circuitry 41 is configured to run one or several computer program(s) or software (SW) 43 stored in a storage 42 of one or several storage unit(s) e.g. a memory. The storage unit is regarded as a computer readable means 42, forming a computer program product together with the SW 43 stored thereon as computer-executable components and may e.g. be in the form of a Random Access Memory (RAM), a Flash memory or other solid state memory, or a hard disk, or be a combination thereof. The processing circuitry 41 may also be configured to store data in the storage 42, as needed. The camera module 400 may also comprise a communication interface for communicating with entities external to the module 400, e.g. with a computer functioning as a controller of the modelling system 100.

Figure 4A:
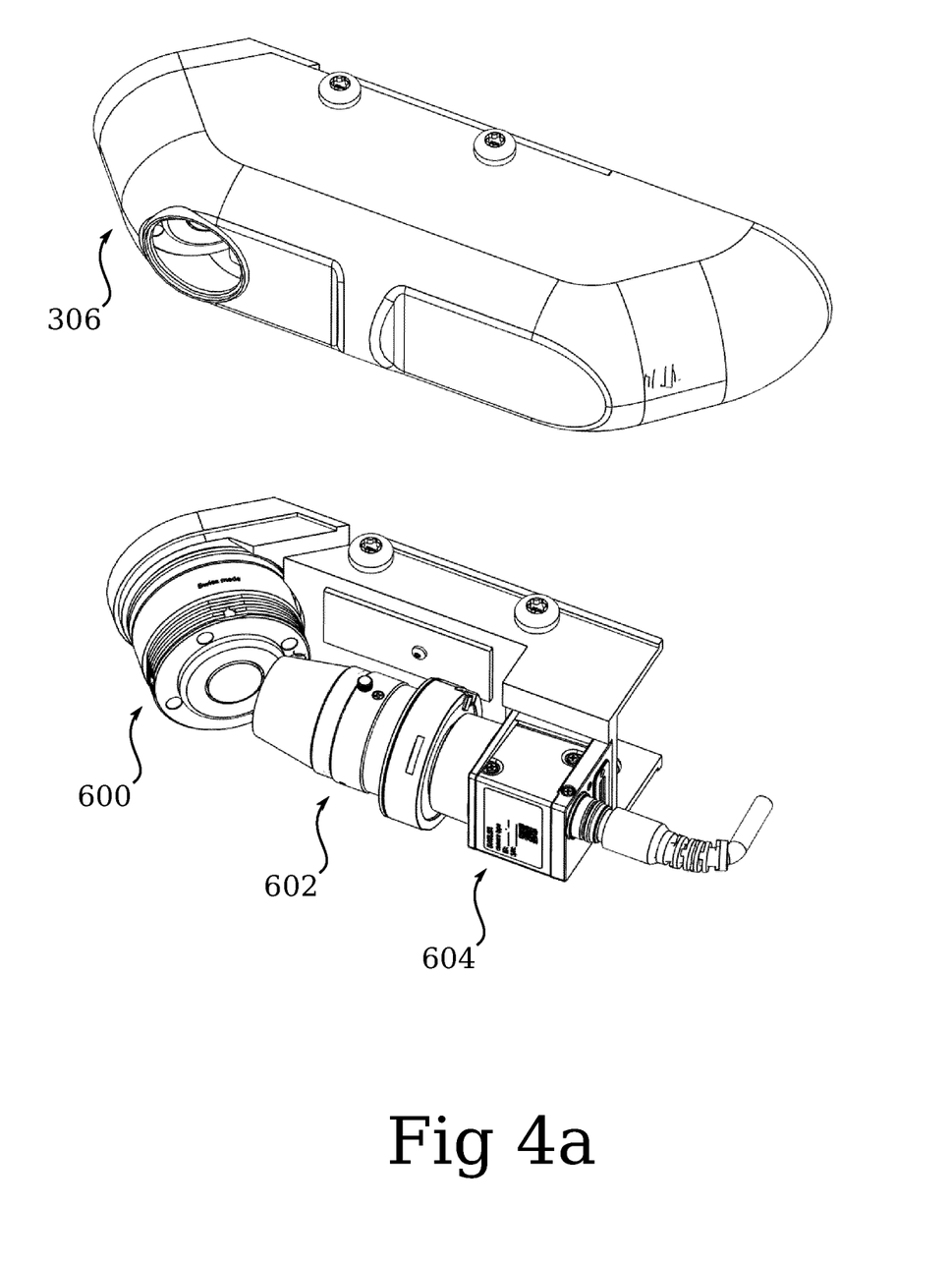
FIG. 4a illustrates a visible-light camera, in accordance with some embodiments of the present invention.

FIG. 4a illustrates a visible-light camera 306, e.g. a high-resolution colour camera. Such a camera can comprise a movable mirror 600, the movement of which may be controlled and actuated by means of electromagnetic force, e.g. my means of an actuator comprising a coil similar to a voice coil in a speaker. The mirror is used for selecting the part of the surface of the body B which should be imaged by allowing light from that part of the surface to be reflected on the mirror 600 and pass through the focusing lens 602 to the camera sensor 604. The electronic camera sensor 604 is arranged to produce a digital image of the surface part as focused thereon by the focusing lens 602 via the mirror 600.

The focusing lens 602, e.g. an actuated lens, can be controlled by a computer e.g. using the model previously obtained by means of the 3D modelling device. In an embodiment, a scanning plan has been created to cover the whole body B of the subject, using multiple high-resolution cameras 306 of respective multiple camera modules 400. This scanning plan may schedule the field of view (set by using and moving the mirror 600) and the focus (set by using the lens 602) in part based on the model (which may include individual features of the specific body) but also in part based on positions of the available cameras and the desired overlap to stitch the images. For each camera 306, focusing can be speeded up by setting a new focus while the mirror 600 is still moving.

When the 3D structure of the surface part to be imaged is known, e.g. by means of the 3D modelling device 302, for instance if the 3D modelling device provides a plurality of distances to each surface part to enable modelling of the topography of the surface part, the number of focus steps, and the distance therebetween (density), needed to cover the depth of focus desired may be calculated. For example, a skin segment with a higher variation of topography may require more focus steps (e.g. in combination with smaller pitches), and thus more stacked images, to resolve specific features. The topographic model may also be used to define the different, typically adjacent, surface parts. For example, if the field of view (FOV) of a camera in one of the camera modules 400 in the system 100 is occluded, as determined from the topographic model, then another one of the camera module(s) 400 in the system 100, with an overlapping FOV but with a different angle to the surface part of interest may be used instead, to avoid the occlusion.

The first focus can be set at the same time as the mirror is moved to cover the surface part to minimize total scan time. The first focus may be set to slightly above the surface. When the mirror has been positioned, a series of consecutive stacked images may be taken, one (or more than one e.g. for super-resolution) per focus step, moving the focus further into the surface/skin, to capture a stack of images. The stack may then be merged by using a focal plane merging algorithm. Focal plane merging combines multiple images taken at different focus distances to give a resulting image with a depth of field greater than the depth of field available from the camera itself. The focal plane merging algorithm may use image features and their sharpness but also the 3D information of the surface part, e.g. from the 3D modelling device 302, to improve quality of the merged image. High-speed focusing by the focusing lens 602 may be possible for the visible-light camera 306, especially if it uses a liquid lens, which can change shape quickly. A liquid lens incorporates optical grade liquid in the middle of a cell structure and works more like the lens of an eye when able to change shape. Additionally or alternatively, a liquid lens can change focus by being moved to change its distance to the sensor, just like a regular solid lens. The liquid allows the lens itself to move and change shape, either mechanically or electronically, benefitting both focusing speed and the focal length that can be achieved.

The schedule based on the model can then be used to select the next field of view for the visible-light camera 306 to cover the next surface part of the test subjects body B. The known parallax between the structured light scanner 302 and the visible-light camera 306 may be used to stitch the image stacks into a full visible-light image of the surface/skin of the body. Any base overlap is known from the mirror position selected based on the model. The stitching may then be finetuned using the overlap between two image stacks, using for example optical flow, template matching or feature matching.

Figure 4B:
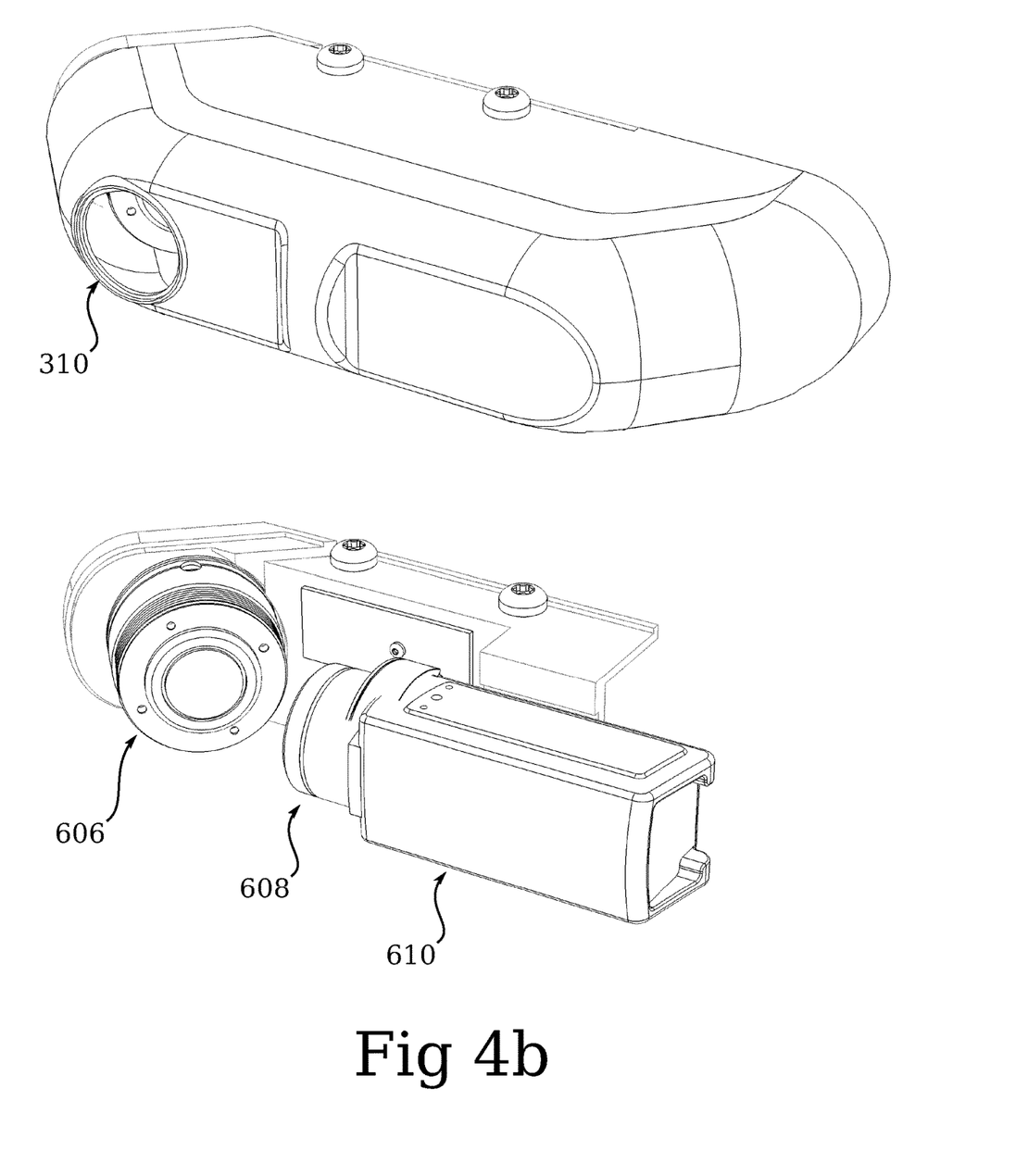
FIG. 4b illustrates a thermal camera, in accordance with some embodiments of the present invention.

FIG. 4b illustrates a thermal camera 310. Such a camera may comprise a movable mirror 606, e.g. a metal mirror suitable for infrared light, the movement of which mirror may be controlled and actuated by means of electromagnetic force, e.g. my means of an actuator comprising a coil similar to a voice coil in a speaker. As for the visible-light camera 306, the mirror may be used for selecting the part of the body surface which should be imaged and infrared light from that part of the surface is reflected on the mirror 606 to pass through the focusing lens 608 to the thermal camera sensor 61o. Alternatively, the thermal camera may have a wider field of view not requiring a movable mirror.

In contrast to the visible-light camera, infrared light cannot be focused using liquid lenses. Thus, the focusing lens 6o8 of the thermal camera typically comprises movable solid, e.g. glass, lenses and the focusing time is longer. This makes it even more advantageous to use the obtained distances to the surface parts to set the desired focus depth before a thermal image is taken. The thermal images are not stacked and it speeds up the acquisition time if a thermal image is being correctly focused while the mirror 6o6 is moved. The discussion above for a visible-light camera 306 relating to stacked images may also be relevant to some embodiments the thermal camera 310.

Figure 5:
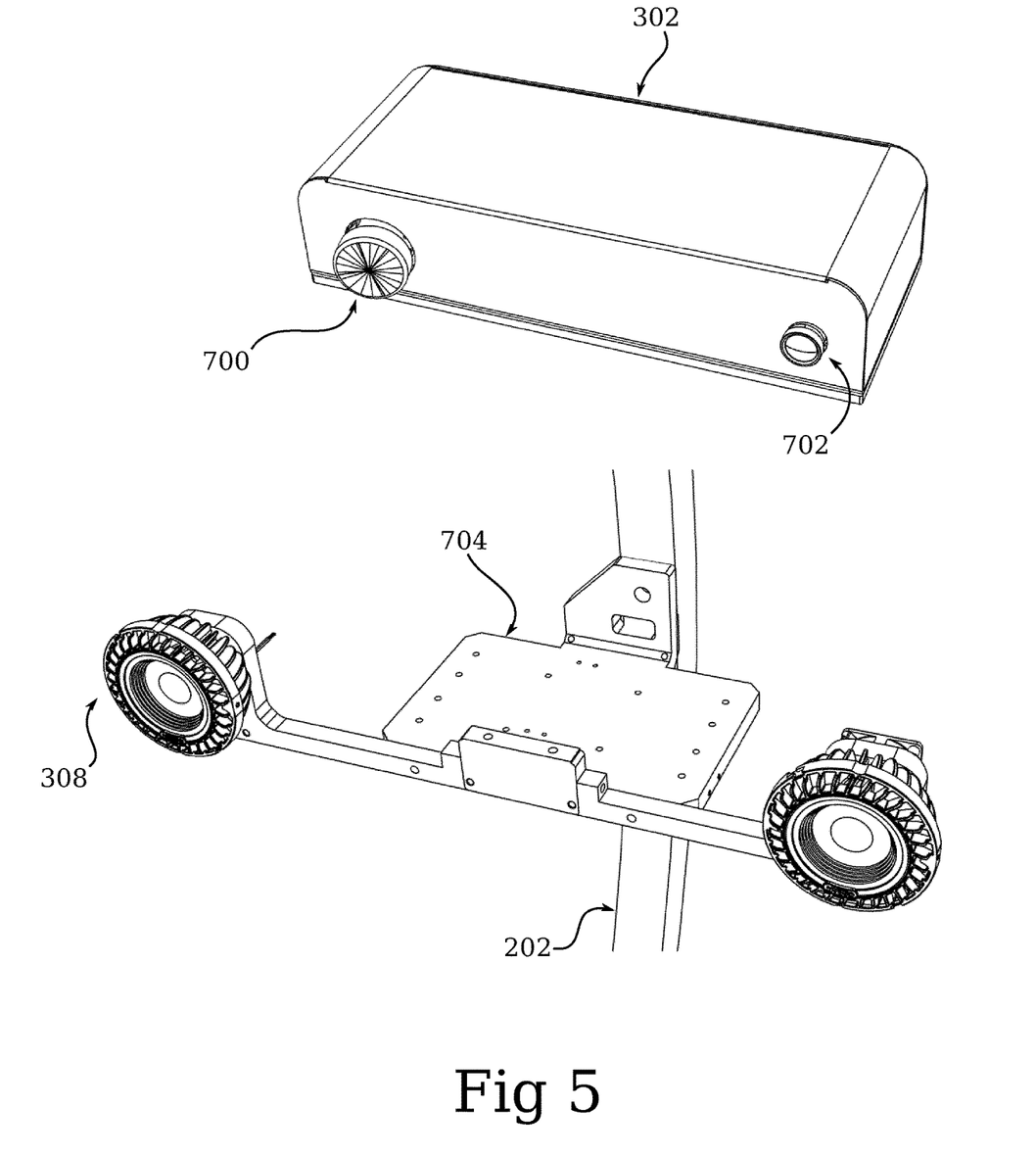
FIG. 5 illustrates an embodiment of a structured-light scanner, as an example of a 3D modelling device, optionally combined with light fixtures, in accordance with some embodiments of the present invention.

FIG. 5 illustrates a 3D modelling device 302, e.g. a 3D or depth camera such as comprising a structured-light scanner and/or time-of-flight camera and/or a stereo camera e.g. with a structured light or random dot projector. Herein, the 3D modelling device 302 is exemplified with a structured-light scanner. The structured light scanner 302 comprises a camera 700 and structured light projector 702. The structured light scanner 302 may be mounted on the fixture 704 of the camera module 400. High-intensity light-emitters 308 may be mounted on the same fixture. The fixture may be mounted on a structural support beam 202.

In some embodiments, the 3D modelling device 302 of each, or at least one of, the camera modules 400 in the modelling system 100, or an additional imaging system in the modelling system 100 but external to the camera modules 400, may comprise a low-resolution, and thus higher FOV, 3D imaging system, e.g. operating in a non-visible light spectrum, which system may operate during the acquiring of images of the surface of the body B. By means of the low-resolution 3D imaging system, body movements between image acquisition of different surface parts (with any camera 306 and/or 310 in the camera module 400) may be compensated for. Also stitching together of the sequentially acquired images may be facilitated. Such an additional imaging system may comprise several 3D cameras, typically less than the number of camera modules 400 in the modelling system 100.

Figure 6:
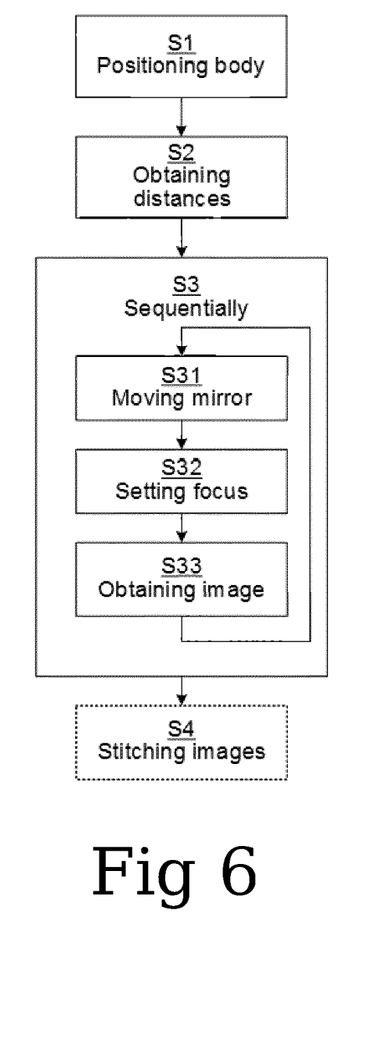
FIG. 6 is a flow chart illustrating some embodiments of a method performed by a camera module, in accordance with some embodiments of the present invention.

FIG. 6 is a flow chart illustrating a method of the present invention. The method is performed by a camera module 400 of the present disclosure. Prior to the performing of the method, the body B may be positioned S1 in relation to the camera module 400, e.g. by moving the body and/or the camera module. The method comprises, by the 3D modelling device 302, obtaining S2 the respective distances to the adjacent parts of the surface of the body B positioned S1 in relation to the camera module 400. The method then further comprises sequentially S3, for each of the surface parts: automatically moving S31 the mirror 600 and/or 606 to direct light from the surface part into the focusing lens 602 and/or 608; by the focusing lens 602 and/or 608, during the moving S31 of the mirror 600 and/or 606, automatically setting S32 the focus on the surface part based on the obtained S2 distance to said surface part; and, by the camera sensor 604 and/or 610, acquiring S33 the image of the surface part. Preferably, each of the acquired S33 images extends some distance around the surface part, resulting in an overlap between the images which may facilitate stitching S4 to obtain a sectional image of the section of the body surface covered by the camera 306 and/or 310. In some embodiments, the method further comprises stitching S4 the sequentially S3 acquired S33 images to acquire a sectional image of the surface of the body B.

In some embodiments of the present invention, the obtaining S2 of the distances comprises, for each of the surface parts, obtaining a plurality of distances to the surface part and obtaining the spatial model, at least in part, by modelling a topography of the surface part based on said plurality of distances. Then, in some embodiments, the setting S32 of the focus comprises setting the focus based on said topographic model. In some embodiments, the setting S32 of the focus comprises calculating the number of distances of said plurality of distances to which the focus is set, and/or the focus pitch(es) therebetween, based on the topographic model of the surface part. Additionally or alternatively, in some embodiments, the obtaining S2 of the respective distances comprises defining the surface parts based on the topographic model.

Regarding the system 100 comprising a plurality of camera modules 400, each module 400 may be arranged for acquiring S33 the images of the different parts of a respective section of the surface of the body B. The respective sections of the modules may be overlapping, and as with the different parts of each section, also the sectional images may be stitched together to form a system-wide image, typically overlayed on a similarly stitched together spatial model of the surface of the body.

The system 100 may be arranged with modules 400 with respective overlapping sections covering at least 180° of the body B, typically a front or back side of the body. To obtain a full body image covering the whole surface of the body, the body B, or the system 100, may then have to be turned 180° once and the two system-wide images may be stitched together. Any suitable number of modules 400 may be comprised in the system 100, e.g. to cover a front or back side of the body B, such as a number of modules 400 within the range of 4-20 modules 400. In a currently preferred embodiment, nine modules 400 are comprised in the system 100, e.g. arranged in a 3×3 matrix.

As mentioned above, a topographic model may be obtained for each module 400 by means of the 3D modelling device 302 of said module 400. Similarly to the stitching together of different sectional images to form a system-wide image, also the topographic model for each section (i.e. obtained S2 by each module 400) may additionally or alternatively be stitched together to form a system-wide topographic model, e.g. covering a front or back side of the body B. In some embodiments, this system-wide topographic model may be used to define the respective sections of the camera(s) 306 and/or 310 of each of the modules 400, i.e. defining the borders of the section divided into the adjacent parts of which images are acquired S33. This enables accounting for individual differences of each body B to which the system 100 is applied, specifically differently shaped bodies B. Due to different shapes of bodies B, the field of view of a camera 306 or 310 may differ from one body to another, e.g. due to occlusion as mentioned above, and the respective sections covered by the different modules 400 may be adjusted accordingly for each body B.

Additionally or alternatively, a low-resolution 3D imaging system (as mentioned above) may be used for obtaining the system-wide topographic model. The low-resolution 3D imaging system typically has a larger field of view (FOV) than the 3D modelling devices 302 which typically have a higher resolution. For instance, the low-resolution 3D imaging system may be used for defining respective surface sections of the body for the 3D modelling device 302 of each module 40o, and the stitched-together system-wide topographic model obtained from the 3D modelling devices 302 may be used for adjusting said sections to sections for the camera(s) 306 and/or 310 of each of the modules 400. The sections are preferably overlapping to facilitate stitching. Additionally or alternatively, the lower resolution 3D information obtained by means of the low-resolution 3D imaging system, which covers a larger part of the body surface than the 3D modelling devices 302 by virtue of its larger FOV, may be used to facilitate the stitching-together of the respective spatial or topographic models of the 3D modelling devices 302 to obtain the system-wide spatial or topographic model. Thus, the low-resolution 3D imaging system may provide a general map for stitching-together the sectional but higher-resolution spatial or topographic models of the 3D modelling devices 302.

Figure 7:
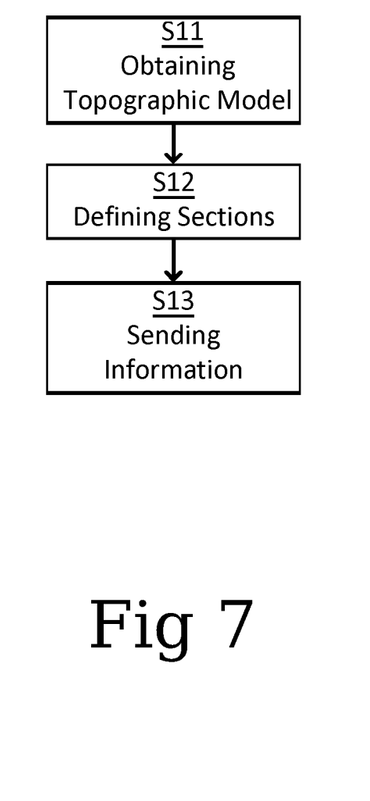
FIG. 7 is a flow chart illustrating some embodiments of a method performed by a modelling system, in accordance with some embodiments of the present invention.

FIG. 7 illustrates some embodiments of a method performed by the system 100. The method comprises, by the 3D modelling devices 302 of the camera modules 400, obtaining S11 a system-wide topographic model of the surface of the body B positioned in relation to the modelling system 100. Typically, respective topographic models of the 3D modelling devices 302 of all the camera modules 400 in the system 100 are stitched together to the system-wide topographic model. Based on the obtained S11 system-wide topographic model, a respective surface section for the at least one camera 306 and/or 310 of each of the camera modules 400 is defined S12. Thus, depending on the individual shape of the body B, the different sections of the body surface to be covered by the camera(s) of each module 400 may be defined. Then, information about the defined S12 sections are sent to the camera modules for use thereby, e.g. in accordance with the method discussed in relation to FIG. 6, where the surface section assigned to a camera module is divided into the adjacent parts discussed therein. The obtaining S2 of the distances to the adjacent surface parts may typically be done as part of the obtaining S11 of the system-wide topographical model. Alternatively, the obtaining S2 of the distances to the adjacent surface parts may be done after the defining S12 of the sections and sending S13 of information thereof to the modules 400.

In some embodiments, the obtaining S11 of the system-wide topographic model comprises obtaining the system-wide topographic model by means of a low-resolution 3D imaging system comprised in the modelling system 100. Thus, a low-resolution 3D imaging system may be used in addition to the 3D modelling devices 302 of the camera modules 400, e.g. as discussed above, to obtain the system-wide topographic model. The low-resolution 3D imaging system has a lower resolution and a larger field of view than each of the 3D modelling devices 302.

The present disclosure has mainly been described above with reference to a few embodiments. However, as is readily appreciated by a person skilled in the art, other embodiments than the ones disclosed above are equally possible within the scope of the present disclosure, as defined by the appended claims.

The invention claimed is:

1. A camera module, comprising:
a 3D modelling device for obtaining respective distances to a plurality of adjacent parts of a surface of a body;
a camera arrangement for acquiring images of the parts of the surface, wherein the camera arrangement comprises at least one camera, comprising:
a camera sensor for producing said images,
a focusing lens for focusing light reflected on the surface of the body onto the camera sensor, and
a movable mirror for receiving light reflected from the surface of the body and sequentially selecting respective parts of the surface of the body by directing the light reflected from said respective parts of the surface into the focusing lens; and
a housing enclosing both the 3D modelling device and the camera arrangement;
wherein the focusing lens is adapted to automatically set the focus of the camera during the moving of the mirror based on the obtained distances, and
wherein the camera module is mounted on a frame for being in a fixed spatial relationship to the body.

2. The camera module of claim 1, wherein the at least one camera comprises or consists of a visible-light camera or a thermal camera, or a visible-light camera and a thermal camera.

3. The camera module of claim 1, wherein the at least one camera comprises a visible-light camera, the focusing lens of which is a liquid lens.

4. The camera module of claim 1, wherein the 3D modelling device comprises a structured-light scanner and/or a time-of-flight camera and/or a stereo camera.

5. A modelling system, comprising:
the frame; and
a plurality of the camera modules of claim 1, fixed in relation to each other on the frame;
wherein the modelling system is arranged to receive the body to be modelled such that the modules are mounted on the frame in a fixed spatial relationship to the body.

6. The modelling system of claim 5, further comprising a low-resolution 3D imaging system external to the camera modules.

7. A method performed by the camera module of claim 1, the method comprising:
positioning a body in a fixed spatial relationship to a camera module;

by a 3D modelling device, obtaining respective distances to adjacent parts of a surface of the body, positioned in relation to the camera module; and sequentially, for each of the parts of the surface of the body:
- automatically moving a mirror that receives light reflected from the surface of the body to select respective parts of the surface of the body by directing the light from the respective part of the surface into a focusing lens,
- by the focusing lens, during the moving of the mirror, automatically setting a focus on the surface part based on the obtained respective distance to said surface part, and
- by a camera sensor of the camera module, acquiring an image of the surface part.

8. The method of claim 7,
wherein the setting of the focus comprises sequentially setting the focus to a plurality of distances from slightly above the surface to slightly below the surface; and
wherein the acquiring of the image comprises acquiring a plurality of stacked images, at least one per each of the plurality of distances, and merging the stacked images to acquire the image having an increased depth of field.

9. The method of claim 7, wherein the obtaining of the distances comprises obtaining a spatial model, comprising a point cloud, of the surface of the body.

10. The method of claim 9,
wherein the obtaining of the distances comprises, for each of the surface parts, obtaining a plurality of distances to the surface part, and the obtaining of the spatial model comprises modelling a topography of the surface part based on said plurality of distances to obtain a topographic model, and
wherein the setting of the focus comprises setting the focus based on said topographic model.

11. The method of claim 10, wherein the setting of the focus comprises calculating the number of distances of said plurality of distances to which the focus is set, and/or the focus pitch therebetween, based on the topographic model of the surface part.

12. The method of claim 10, wherein the obtaining of the respective distances comprises defining the surface parts based on the topographic model.

13. The method of claim 7, further comprising stitching the sequentially acquired images for each of the parts of the surface of the body to acquire a sectional image of the surface of the body.

14. The method of claim 7, wherein the body is a live body of a human or animal subject.

15. The camera module of claim 1, wherein the movable mirror sequentially directs light according to a scanning plan and the scanning plan is based in part on the camera arrangement.

* * * * *